United States Patent
Lindström et al.

(12)

(10) Patent No.: US 10,977,925 B2
(45) Date of Patent: Apr. 13, 2021

(54) DISPLAY SYSTEM FOR USAGE COMPLIANCE OF HYGIENE EQUIPMENT

(71) Applicant: ESSITY HYGIENE AND HEALTH AKTIEBOLAG, Gothenburg (SE)

(72) Inventors: Håkan Lindström, Gothenburg (SE); Jenny Logenius, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

(21) Appl. No.: 16/303,269

(22) PCT Filed: May 30, 2016

(86) PCT No.: PCT/EP2016/062155
§ 371 (c)(1),
(2) Date: Nov. 20, 2018

(87) PCT Pub. No.: WO2017/207019
PCT Pub. Date: Dec. 7, 2017

(65) Prior Publication Data
US 2019/0206226 A1   Jul. 4, 2019

(51) Int. Cl.
*G08B 21/24* (2006.01)
*G16H 40/20* (2018.01)
*G06Q 10/06* (2012.01)
*G06F 16/22* (2019.01)

(52) U.S. Cl.
CPC ......... *G08B 21/245* (2013.01); *G06Q 10/063* (2013.01); *G16H 40/20* (2018.01); *G06F 16/22* (2019.01)

(58) Field of Classification Search
CPC .............................. G08B 21/245; G16H 40/20
USPC ....................................................... 340/573.1
See application file for complete search history.

(56) References Cited

U.S. PATENT DOCUMENTS

| | | | |
|---|---|---|---|
| 8,294,584 B2 * | 10/2012 | Plost .................... | G08B 21/245 340/500 |
| 8,786,429 B2 * | 7/2014 | Li ............................. | G01S 5/02 340/539.13 |
| 9,881,485 B2 * | 1/2018 | Hajdenberg ......... | G08B 21/245 |
| 2002/0061500 A1 * | 5/2002 | Collopy ............. | G09B 19/0076 434/238 |
| 2009/0224924 A1 * | 9/2009 | Thorp .................... | G16H 40/20 340/573.1 |

(Continued)

OTHER PUBLICATIONS

International Preliminary Report on Patentability dated Dec. 13, 2018 for PCT/EP2016/062155.

(Continued)

*Primary Examiner* — John A Tweel, Jr.
(74) *Attorney, Agent, or Firm* — Wood Herron & Evans LLP

(57) ABSTRACT

Displaying an indicator of a usage of hygiene equipment by one or more operators, the system including a first receiving section configured to receive usage data from an equipment sensor arrangement, said usage data indicating a usage of said hygiene equipment; a calculation section configured to determine, based on said usage data said indicator; and an output section configured to provide display data to a display unit based on said indicator, said display unit being arranged so as to convey said display data to said one or more operators.

15 Claims, 5 Drawing Sheets

(56) References Cited

U.S. PATENT DOCUMENTS

| | | | |
|---|---|---|---|
| 2011/0193703 A1* | 8/2011 | Payton | G08B 21/245 340/573.1 |
| 2013/0027199 A1 | 1/2013 | Bonner | |
| 2013/0342349 A1 | 12/2013 | Cruz | |
| 2016/0005328 A1 | 1/2016 | O'Toole et al. | |
| 2018/0286215 A1* | 10/2018 | Christensen | G08B 21/245 |

OTHER PUBLICATIONS

European Office Action issued in European patent application No. EP 16 726 537.0, dated Aug. 21, 2020.

* cited by examiner

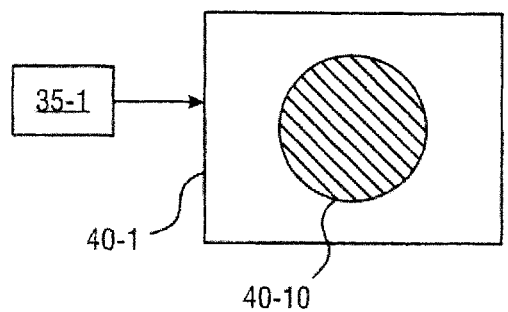
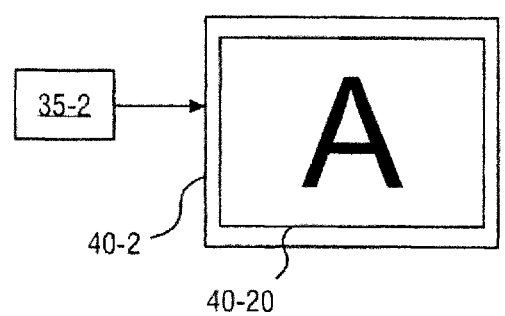
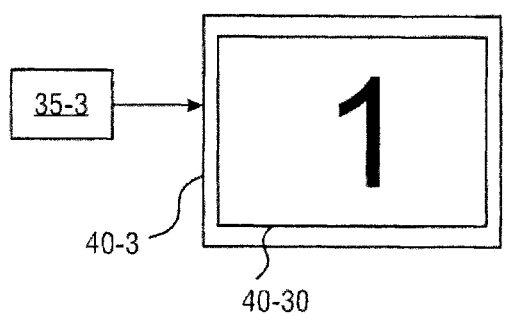
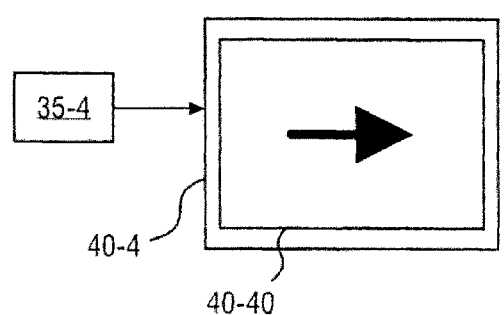
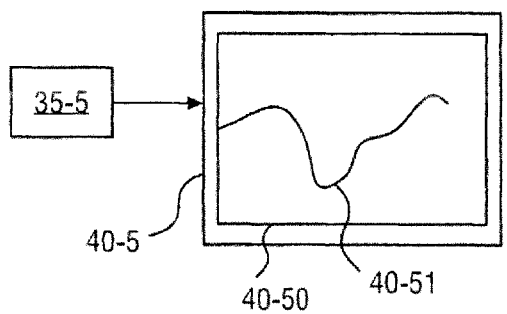
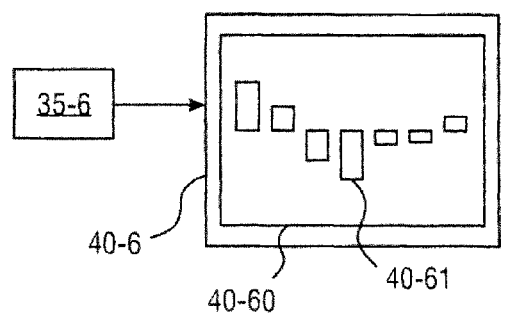
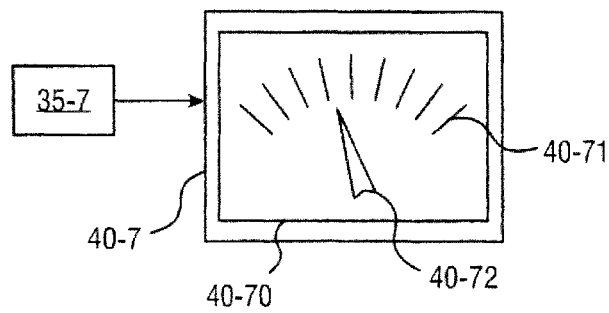

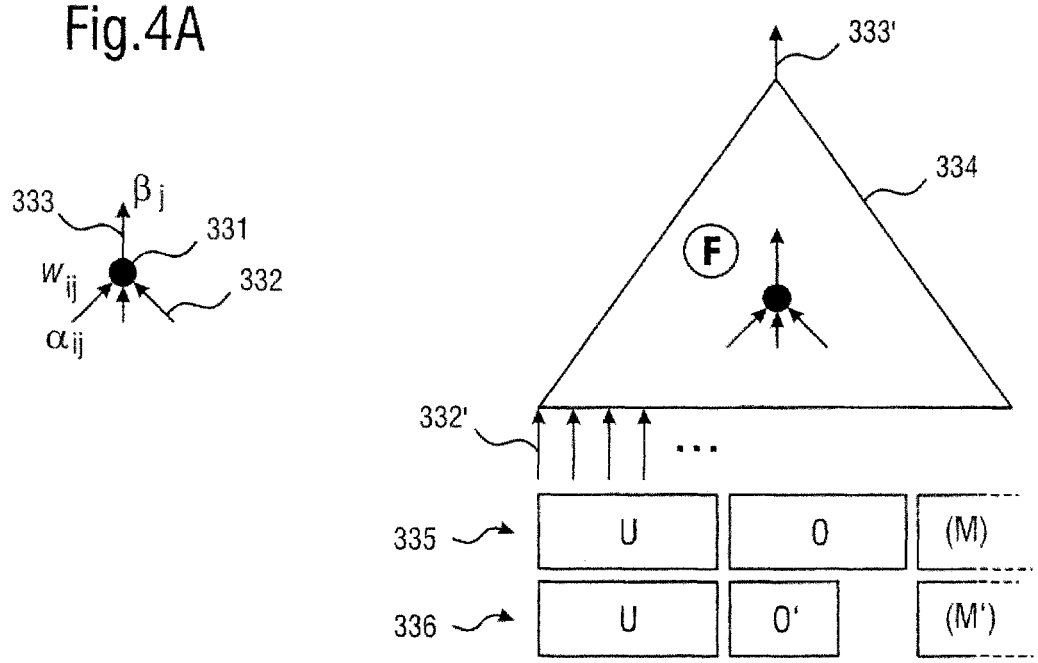
Fig. 4A
Fig. 4B
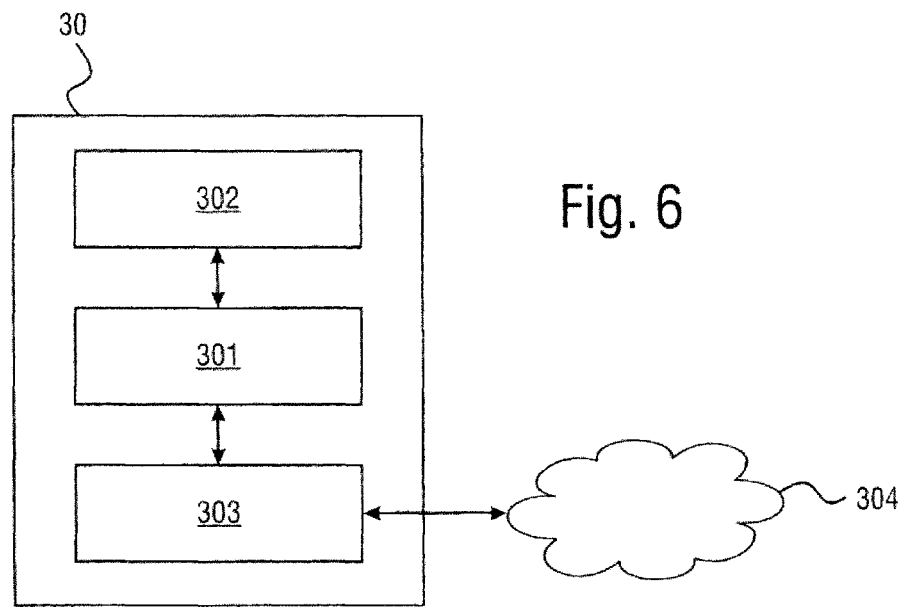
Fig. 6

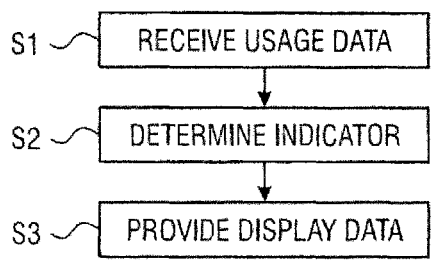
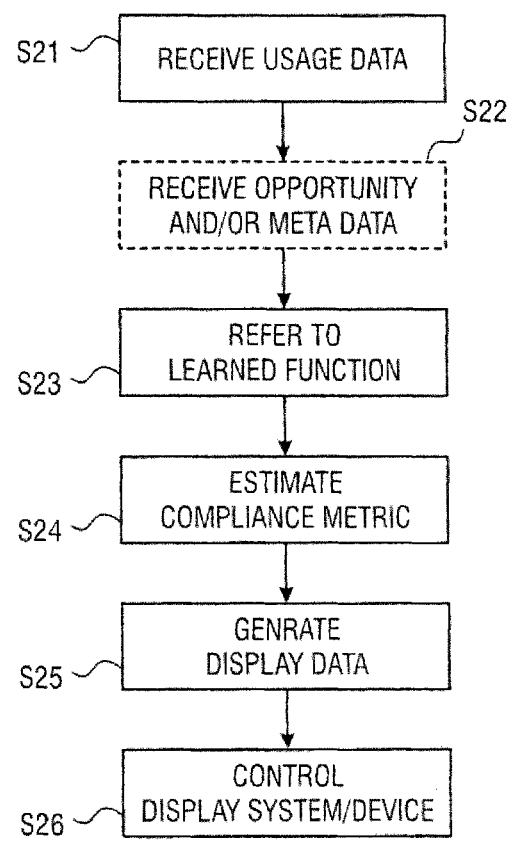
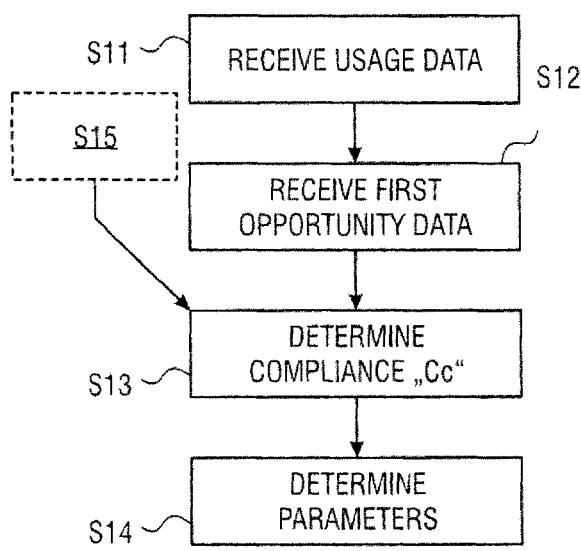
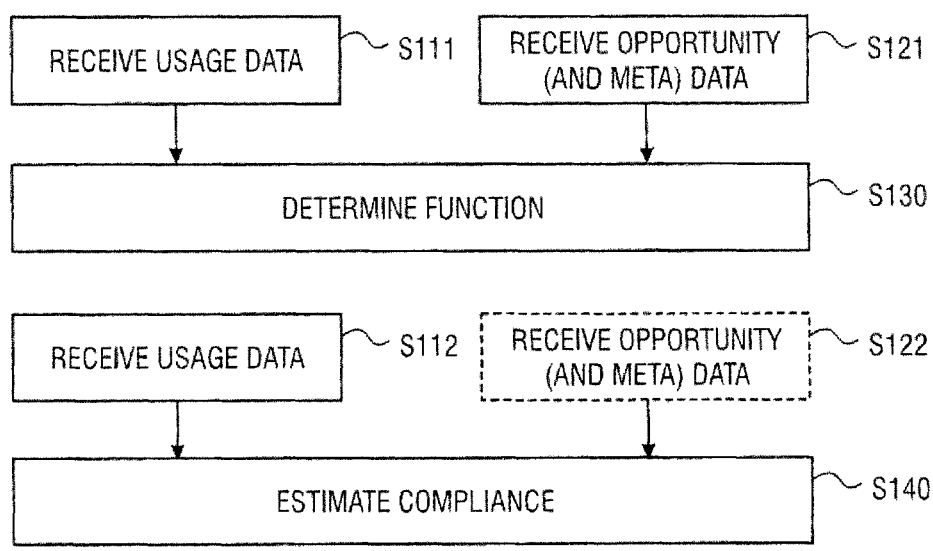

DISPLAY SYSTEM FOR USAGE COMPLIANCE OF HYGIENE EQUIPMENT

CROSS-REFERENCE TO PRIOR APPLICATION

This application is a § 371 National Stage Application of PCT International Application No. PCT/EP2016/062155 filed May 30, 2016, which is incorporated herein in its entirety.

TECHNICAL FIELD

The present disclosure generally relates to estimating a compliance metric in the context of hygiene equipment, such as soap, disinfectant, and/or towel dispensers, and the like. More particularly, the present disclosure relates to ways of conveying specific forms of values for such compliance metric estimate that can promote the actual usage of hygiene equipment by corresponding operators.

BACKGROUND

Hygiene equipment is commonplace today in many facilities, such as hospitals, medical service centers, intensive care units, day clinics, private practices, lavatories, rest rooms, hotels, restaurants, cafes, food service places, schools, kindergartens, manufacturing sites, administration and office buildings, and, in general, places and facilities that are accessible to the public or to a considerable number of individuals. The mentioned hygiene equipment thereby includes various types of individual devices and installations such as soap dispensers, dispensers for disinfectant solutions, gels or substances, towel dispensers, glove dispensers, tissue dispensers, hand dryers, sinks, radiation assisted disinfectant points, ultraviolet (UV) light, and the like.

Although such hygiene equipment is commonplace today in many places, the use thereof by the individuals visiting these places or working in these places is still oftentimes not satisfactory. For example, hospitals, and, in general, medical service centers often suffer from hygiene deficiencies, which, in turn, may lead to the spread of infections and related diseases. In particular, such insufficient hygiene amongst medical care personnel coming into close contact with patients and bodily fluids can lead to the spread of infectious diseases amongst the personnel and other patients. It is also known that infections by highly resistant bacteria pose a severe problem in such places, especially in hospitals. In general, so-called Healthcare Associated Infections (HAI) are a real and tangible global problem in today's healthcare. HAI can be found to be currently the primary cause of death for 140.000 patients/year, affecting millions more and costs society in the range of billions of EUR/year.

At the same time, however, it is known that hygiene, and, in particular, hand hygiene, is an important factor as far as the spread of infectious diseases are concerned. Specifically, medical care personnel should make proper use of hand hygiene as often as possible so that the spread of bacteria and other disease causing substances is minimized. The actual usage of such hygiene equipment, however, may depend on—amongst others—the management of the facility, accessibility and usability of the equipment, culture, the cooperation and will exercised by the individuals working in these places or visiting such places, training of individuals, time pressure and possibly also other factors. In other words, an important factor remains the fact that individuals may not make use of installed and provided hygiene equipment although they are supposed to. Furthermore, it is generally accepted that an increased use of hygiene equipment can substantially contribute in reducing the spread of bacteria and the like, which, in turn, can drastically reduce the appearance of related infections and diseases.

For example, a corresponding relatively low compliance metric may indicate that the actual use of hygiene equipment is not satisfactory, whilst relatively high compliance metric may indicate that the actual use of hygiene equipment corresponds, within a given threshold, to some target usage, and, consequently, may be regarded as being satisfactory. Such a compliance metric may provide many advantages, since it gives a concise picture to operators of the corresponding facility so that they may initiate measures for increasing the actual use of hygiene equipment.

Therefore, there are already ways of estimating such a compliance metric in the arts, wherein the conventional approaches usually rely on measuring and/or observing "manually" by a human observer so-called opportunities and comparing these obtained opportunities to a measured/detected/observed actual use of the hygiene equipment. In other words, the opportunities indicate any event when hygiene equipment should or could have been used. By then comparing this "should/could"-value to an actual usage value a compliance metric can be calculated, as e.g. a percentage value or a ratio. In general, the opportunities can be well defined figures, since they may be associated to specific rules and/or recommendations. For example, the World Health Organization (WHO) has defined the so-called "Five Moments Of Hand Hygiene" (cf. www.who.int/psc/tools/Five_moments/en/) including as explicit definitions for opportunities: 1. Before patient contact; 2. Before aseptic task; 3. After body fluid exposure risk; 4. After patient contact; and 5. After contact with patient surroundings. Moreover, measurements on a corresponding hand hygiene compliance is becoming a regulatory requirement for the healthcare sector and may serve as an important quality improvement tool.

As a consequence, one may have considerable interest in that a given or desired target compliance is achieved. In other words, there is considerable interest that the individuals (operators) that are involved with such facilities implement the hygiene scheme as good as possible so as to reduce the spread of any disease as effectively as possible. At the same time, however, the actual use of hygiene equipment may quite considerably depend on the cooperation shown by the individuals.

There is therefore a need for an improved system and method of promoting the use of hygiene equipment so that preferably a target use compliance is achieved and the spread of diseases is substantially reduced, whilst the implementation of the system should interfere as little as possible with existing surroundings, such as the mentioned hospitals, wards, and related facilities.

SUMMARY

According to one aspect, there is provided a system displaying an indicator of a usage of hygiene equipment by one or more operators. The system includes a first receiving section configured to receive usage data from an equipment sensor arrangement, said usage data indicating a usage of said hygiene equipment; a calculation section configured to determine, based on said usage data said indicator; and an output section configured to provide display data to a display unit based on said indicator, said display unit being arranged so as to convey said display data to said one or more operators.

According to another aspect, there is provided a method for displaying an indicator of a usage of hygiene equipment by one or more operators. The method includes receiving usage data from an equipment sensor arrangement, said usage data indicating a usage of said hygiene equipment; determining, based on the received usage data said indicator; and providing display data to a display unit based on said indicator, said display unit being arranged so as to convey said display data to said one or more operators.

BRIEF DESCRIPTION OF THE DRAWINGS

Embodiments of the present invention, which are presented for better understanding the inventive concepts but which are not to be seen as limiting the invention, will now be described with reference to the figures in which:

FIGS. 2A to 2G show schematic views of different embodiments of display units and display systems;

FIGS. 4A and 4B show schematic views in conjunction with a neural network being used for determining a function;

FIG. 5A shows a flowchart of a general method;

FIG. 5B shows a flowchart of a particular way to determine parameters of a function;

FIG. 5C shows a flowchart of a particular way to employ the learned function;

FIG. 5D shows a flowchart of another general method; and

FIG. 6 shows a schematic view of a general entity.

DETAILED DESCRIPTION OF PARTICULAR EMBODIMENTS

Figure 1:
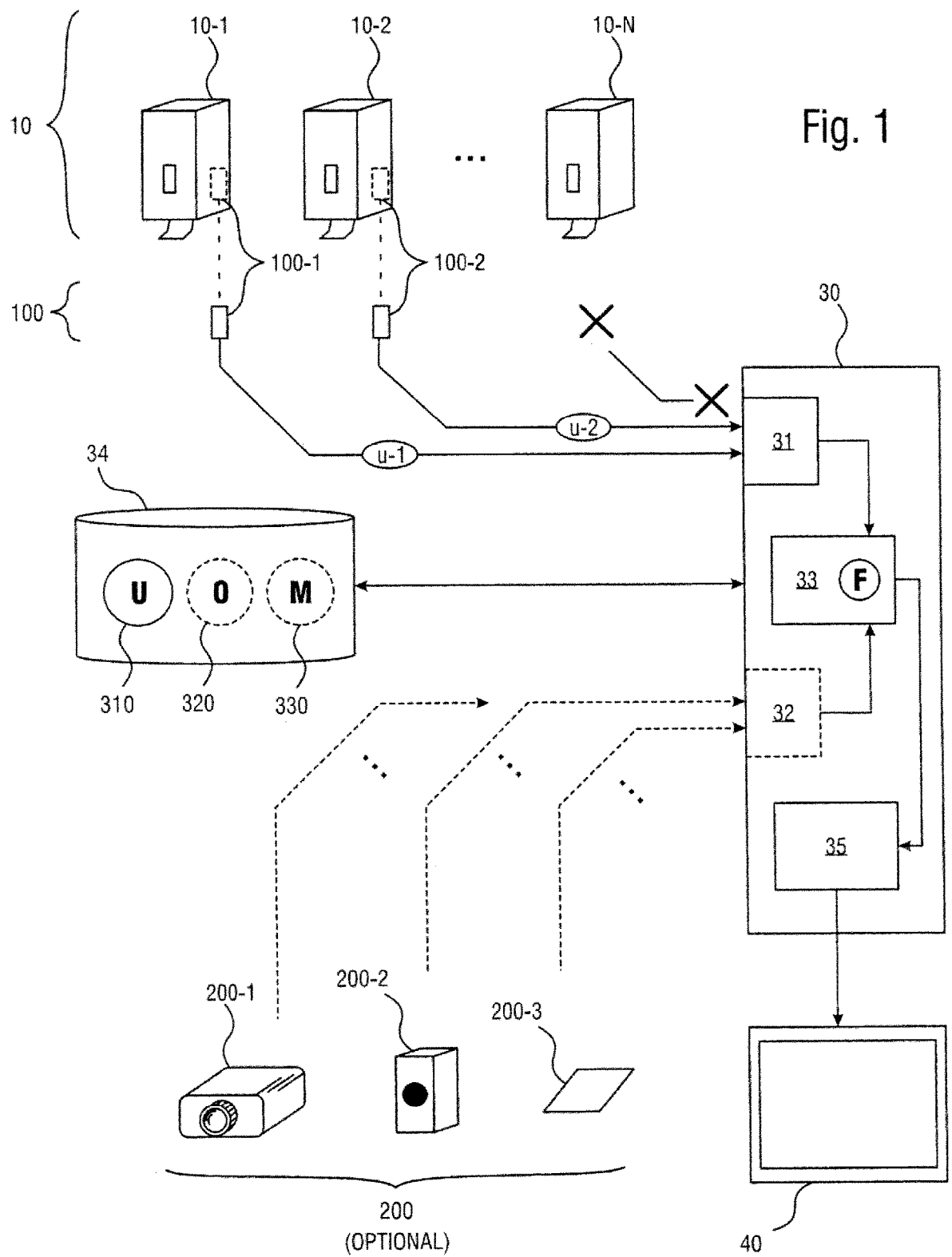
FIG. 1 shows a schematic view of an embodiment of a display system.

FIG. 1 shows a schematic view of an embodiment of a display system. The system is generally deployed for conveying information which can promote the usage of hygiene equipment 10, in the form of, for example, a number of individual pieces of hygiene equipment such as the shown soap or disinfectant dispensers 10-1, 10-2, and 10-N. Generally, the hygiene equipment 10 can include any one of a soap dispenser, a dispenser for disinfectant solutions, gels or substances, a towel dispenser, a glove dispenser, a tissue dispenser, a hand dryer, a sink, a tap, and a radiation assisted disinfectant point, a UV disinfectant apparatus, and the like. Such equipment is generally deployed in a facility being any of a hospital, a medical service center, an intensive care unit, a day clinic, a private practice, a lavatory, a rest room, a hotel, restaurants, cafes, food service places, schools, kindergartens, a manufacturing site, an administration or office building, a shopping center, and, in general, any places and facility that is accessible to the public or to a considerable number of individuals.

The system 30 includes a first receiving section 31 that is configured to receive usage data from the hygiene equipment 10 by an equipment sensor arrangement 100. Said equipment sensor arrangement 100 is a collection of all available sensors that are able to generate and forward individual usage signals u-1, u-2, . . . that indicate an actual use of some or a specific piece of hygiene equipment. For example, a soap dispenser 10-1 may be provided with a sensor 100-1 that is configured to generate a usage signal u-1 whenever an operator actually uses the piece of hygiene equipment and ejects an amount of soap. In this way, the first receiving section 31 receives the usage data in the form of individual signals u-1, u-2, . . . and may thus store the general usage data U as a whole as data 310 in a database 34.

The signals u-1, u-2, . . . are typically signaling "now it happened" (e.g. by carrying a Boolean value "TRUE" or by simply carrying data such as a dispenser ID). In a way, the mere fact that a signal is received may indicate to the system 30 that a usage event happened. However, the signal may also include more information, including information on when the piece of hygiene equipment was used (e.g. timestamp), where it was used (e.g. room or dispenser ID), information on how much of the dispensed substance was used (e.g. dosage size, number of towels etc.), information on who was using it (if the individual operator is tagged and sensed by the system), and/or information on what was used if it is a multi-dispenser containing, for example, both soap and paper.

The data 310 (U) may not be complete in the sense that not every actual usage event may be captured, since not every piece of hygiene equipment may be provided with a corresponding sensor. However, the present embodiment assumes that the captured fraction of usage data is good enough to sufficiently represent the usage of the hygiene equipment. In any way, however, also first and second usage data U, U' may be defined as described in greater detail in conjunction with the corresponding embodiments.

In a general embodiment, the system 30 further includes a calculation section 33 which is configured to determine, based on said usage data an indicator of the usage of the hygiene equipment by the respective operators. The system 30 further includes an output section 35 that is configured to provide display data to a display unit 40 based on said indicator, wherein said display unit 40 is arranged so as to convey said display data to said one or more operators.

This general embodiment takes into account that there may be many ways of deciding what the target use of the hygiene equipment should be. In a way, it can be freely chosen what kind of usage (e.g. consumption) maps to what kind of indicator. In other words, it can be freely chosen up to which usage the indicator may convey via the display data to the operators that usage is satisfactory, or below which other usage the indicator may convey via the display data to the operators that usage should be increased. In other words, it does not matter which way the mapping between the usage and the indicator should be. Rather, this embodiment focuses on freely deciding what the usage should be and that the actual consumption or usage level/rate is observed of a given hygiene equipment. This level/rate will then map to the indicator in respect to the given hygiene "compliance". Hence any change (e.g. an increase or decrease over a given time) to the consumption or usage of the hygiene equipment will be displayed to the operators and be taken as a sign or indication of a change to the usage. The reason for the change of consumption/usage of the hygiene equipment may then be investigated in another step to see if in fact this had anything to do with a change in the operators' behavior or if there were other factors.

In further embodiments, the calculation section 33 may be configured to determine, as said indicator, a compliance metric indicating a usage of the hygiene equipment versus opportunities of using said hygiene equipment. Here, a somewhat more sophisticated calculation is performed where the indicator also considers further details and properties of the observed system. Namely, a compliance metric may be a way of comparing an actual usage of the hygiene equipment to a target usage in the sense of a collection of opportunities when and where the operators should use the hygiene equipment. In a way, such embodiments consider a compliance to given set of usage rules.

For the case of measuring a consumption of hygiene-related consumables (alcohol, soap, towels, and the like) via the so-called usage data, one may contemplate an embodiment where at first a target consumption is observed or determined which would map to a sufficient compliance in the sense of the corresponding consumption, and, with this, use of the hygiene equipment, is assessed as being satisfactory. During operation, the system can then measure the consumption or receive respective usage data and calculate correspondingly the indicator which can then carry information on whether compliance is good or whether compliance is not good in the sense that the operators should use more hygiene equipment in order to improve the hygienic situation. The indicator, in turn, maps to the display data and the resulting display content, which, eventually, conveys to the operators whether the situation is satisfactory or whether they are encouraged to use more hygiene equipment.

According to respective embodiments, the system 30 can additionally include an optional second receiving section 32 which is configured to receive opportunity data O from an opportunity sensor arrangement 200. The opportunity data indicates a set of opportunities to use the hygiene equipment 10 and this opportunity data O is collected by means of receiving individual data signals from corresponding individual pieces of the sensor arrangement 200 such as a camera 200-1, a vicinity and/or door passing sensor 200-2, and the like. Generally, the opportunity sensor arrangement 200 may be any selection of cameras, low resolution cameras (so it may be difficult to identify individuals in the image data), time-of-flight cameras, infrared (IR) cameras, heat/thermo-cameras, micro-phones, image recognition resources, vicinity sensors, radar, ultrasonic sensors, IR sensors, photocell sensor, conductive and/or capacitive sensors (presence, touching), laser range sensors, time-of-flight sensors (e.g. sensors that employ the delay of RF-, e/m-pulse or light signals for determining a location, a distance and/or movements), RFID readers and/or NFC equipment (e.g. also for identifying a badge carried by an operator), door pass sensors, a light barrier, and the like. The collected opportunity data signals are then stored as optional opportunity data O by the system 30 again for example in the database 34 as data 320.

Similar to the signals u-1, u-2, . . . the signals indicating the opportunity data, are typically signaling "now there is/was an opportunity" (e.g. by carrying a Boolean value "TRUE" or by simply carrying data such as a dispenser or location ID). In a way, the mere fact that a signal is received may indicate to the system 30 that there is an opportunity to use some piece of hygiene equipment. However, the signal may also include more information, including information on when the piece of hygiene equipment could have been used (e.g. timestamp), information on how much of the dispensed substance should have been used (e.g. dosage size, number of towels etc.), information on who could have used it (if the individual operator is tagged and sensed by the system), and/or information on what could have been used by the operator if there are alternatives (for example, soap, towel, or disinfectant). As a further or alternative option, also metadata M can be collected and stored as data 330 in the database 34.

In one embodiment, the function F can be determined as a set of correlation parameters that allows for estimating a compliance metric from a given set of the usage data U and possibly also opportunity data O and/or metadata M. A general example is shown in conjunction with the flow chart of FIG. 5A which shows a way to determine parameters of a function. In steps S11 and S12 usage data "U" and corresponding opportunity data "O" are received either sequentially or concurrently (note that the depicted order may likewise be reversed for sequential reception or even made parallel for simultaneous real-time recording so that the first opportunity data is received prior to receiving the usage data). Since the received opportunity data may provide a good quality picture for the actual opportunities, a "complete" compliance metric Cc can be calculated in step S13. The compliance metric Cc corresponds to a best obtainable compliance where a best effort (later to be reduced) is put into obtaining the opportunity data. The compliance metric Cc can be therefore assumed as to be the true compliance metric:

$$Cc=U/O;$$

With the knowledge of Cc, U and O it is then possible to determine parameters of a function F in step S14 which reproduces a compliance metric also without knowledge of opportunity data O, full opportunity data and/or metadata M.

Generally, the opportunity data and the corresponding usage data (usage data or the usage data obtained during at least an overlapping period when the opportunity data was obtained), will allow the calculation of some kind of "complete" compliance metric Cc by employing the arrangements 100 and 200. For example, the data O may indicate for a given period 1000 opportunities, whilst the data U indicates for a corresponding period 920 usage events, so that the complete compliance metric Cc could be calculated to Cc=920/1000=0.92.

The function F can be established e.g. as F(O,U)=Cc with the purpose to reflect the experience from this "known" relationship amongst U, O, and Cc so as to allow an estimation of a compliance rate Ce also from data of lower quality. In this case the "operational" compliance rate can be estimated by relating such less complete data, depending on whether or not also the equipment sensor arrangement is changed for the operation phase relative to the learning phase. In addition to this, the calculation section 33 can also process metadata M that is, however, explained in greater detail in conjunction with the corresponding embodiments.

Generally, the opportunity data O can also indicate a second set of opportunities to use the hygiene equipment 10, wherein the second set of opportunities is reduced relative to the initial set of opportunities that is, at least in part, captured by equipment 200. In other words, the opportunity sensor arrangement operative during an operation phase may be reduced as compared to the opportunity sensor arrangement operative during a learning phase. For example, the sensor equipment 200 may include not only door passing/vicinity sensors 200-2, and the like, but may also include more sophisticated pieces of sensor equipment, such as cameras 200-1. In this way, a relatively more complete opportunity data can be obtained as compared to the relatively less complete opportunity data.

However, a more complex opportunity sensor arrangement may not be desirable to be operated and installed for a longer period of time, since it may be too expensive and/or time consuming to maintain or operate, require legal or ethical approvals or may also be seen as intrusive or not respectful of the personal integrity and therefore require the consent of individuals when, for example, optical and or visual surveillance equipment is used (e.g. cameras 200-1). Whilst the latter may be tolerable for a limited period, some embodiments allow for the general operation of the system 30 without the complex set of opportunity sensor arrangement, and the system 30 can be also advantageously operated by a reduced set of opportunity sensor arrangement, which, in turn, produces reduced opportunity data, or with no opportunity sensor arrangement at all. Embodiments can therefore provide the advantage that the system only needs to be "trained" for a limited amount of time with relatively complex opportunity sensor arrangements, whilst it can be then operated with only relatively simple opportunity sensor arrangements. The embodiments with regard to a "learning phase" and an "operation phase" are explained in greater detail in conjunction with FIGS. 4A and 4B.

In any way, however, the calculation section 33 can be configured, for example, to determine the function F as a product of a machine learning procedure. In such procedures some initial parameters are preset or randomly chosen and the resulting output (here for example the output compliance metric estimate) is compared to a target value that the function F should reproduce for a given set of input data. This is fed back to the procedure that iteratively adjusts the employed parameters so as to match the target output. In a way, during such a machine learning procedure the calculation section 33 can be "trained" so as to determine the suitable parameters.

Machine learning can be generally identified as a set of algorithms and procedures enabling a computing apparatus (computer) to make analysis and predictions based on incomplete data. Many of these algorithms, such as Artificial Neural Networks, are indeed inspired and try to mimic the function of our nerves and brain. A synonym used often alongside machine learning is the so-called "statistical learning" which is a collection of relevant base techniques that are—as such—known and documented e.g. in T. Hastie et al.: "*The Elements of Statistical Learning*" ($2^{nd}$ edition, Springer, ISBN: 978-0-387-84857-0).

As an example, the calculation section 33 can be thus configured to determine the function F as a set of correlation parameters from usage data U acquired for the actual use of the hygiene equipment 10 by the sensor arrangement 100 and the opportunity data O measured/detected by the opportunity sensor arrangement 200 at the same time or during at least in part overlapping intervals. In this way, the opportunity sensor arrangement 200 may at least to some extent provide a sufficient measurement of the opportunities in order to estimate a compliance metric. At least parts of the usage data U and the opportunity data are correlated by these parameters to the compliance, so that also further usage data and, optionally, reduced opportunity data acquired later can be correlated to the compliance by using the parameters of the function.

According to a further embodiment, the equipment sensor arrangement 100-1, . . . includes a first set of equipment sensors and a second set of equipment sensors, and the first receiving section 31 may be correspondingly configured to receive as said usage data first usage data from the first set of equipment sensors and second usage data from the second set of equipment sensors. The calculation section 33 may then also be configured to determine said function based on the first usage data and said first opportunity data, and to estimate said compliance metric from the second usage data and said second opportunity data. In other words, in some embodiments, the equipment sensor arrangement is not necessarily the same for acquiring usage data for determining the function, e.g. during a learning phase, and, respectively, for operating the system for estimating the compliance rate.

As a consequence, the usage data may also be referred to as first usage data and the database 34 further stores second usage data. These embodiments may specifically relate to situations where after the learning phase the number of hygiene equipment or corresponding sensors is reduced, since it may have been determined that it may be enough to have for example only a certain (smaller) number of hygiene equipment (dispensers) equipped with sensors for the purpose of estimating the compliance metric. The equipment sensor arrangement may be considered as being too expensive for later operation and one may want to cut down also on the equipment sensors apart from the opportunity data sensors. As an example, the mentioned second set of equipment sensors may be a part of said first set of equipment sensors, where some sensors of the installed hygiene equipment are simply deactivated (or no longer monitored), or a part of the hygiene equipment is replaced after the learning phase by equipment without sensors and/or connectivity.

In embodiments the system 30 further includes the calculation section 33 so that it is configured to employ the function F, whether determined by the calculation section 33 or not, to determine based on said usage data a compliance metric as some kind of value that represents a current and actual use of the hygiene equipment. In this way, the calculation section can provide information to an output section 35 that is configured to provide display data to a display unit 40 based on said compliance metric, wherein the display unit 40 is arranged to convey said display data to said one or more operators which is explained in greater detail below.

More specifically, the output section 35 may generate the display data in one or more advantageous ways so as to convey information that promotes the usage of the hygiene equipment by the operators in an effective way, which, however at the same time does interfere with the existing surroundings as little as possible. In particular, certain embodiments allow for a way of promoting the use of hygiene equipment by conveying information to the operators in a non-intrusive and more subtle manner. For example, certain embodiments allow for a reduction of distraction by the operators from more critical tasks such as, for example, operating medical equipment in an intensive care unit. In such environments, there will be usually already an abundance of display and operation units. As a consequence, the integration of systems for promoting the use of hygiene equipment may face restrictions and limitations which are, however, advantageously addressed by embodiments.

Related embodiments of display units and display systems are now described in conjunction with FIGS. 2A to 2G. Specifically, these embodiments may allow for a non-intrusive and non-interfering integration into existing environments where hygiene equipment may play an important factor, such as hospital wards, intensive care units, and the like.

Specifically, FIG. 2A shows a schematic view of a display unit 40-1 that is controlled by a respective output unit 35-1. The display unit 40-1 includes a color field 40-10 that is adapted to assume a color by actively emitting corresponding light or by assuming a corresponding color reflecting state (e.g. LCD, LED-Display, OLED-Display, EPD, electrophoretic display, and the like). The output unit 35-1 is here configured to control the display unit 40-1 so as to display a color which is dependent on the compliance metric or indicator determined by the calculation section 33. For example, a first color (e.g. green) may be displayed whenever the indicator or compliance metric is above some given threshold value, whereas a second color (e.g. red) may be displayed whenever the indicator or compliance metric is below some given threshold value. Likewise, the output unit

35-1 may calculate a trend, i.e. a figure indicating an evolution of the indicator or compliance metric over time, and display the first color whenever the trend is positive (i.e. the indicator or compliance metric is rising), whereas the second color may be displayed whenever the trend is negative. Naturally, additional colors or color changing schemes may be employed.

FIGS. 2B, 2C, and 2D show schematic views of display units 40-2, 40-3, and 40-4 that are controlled by respective output unit 35-2, -3, and -4. The display units include displays that are configured to display at least two different characters or symbols. For this purpose, the displays 40-20, -30, and -40 may be implemented as mechanical displays, or again as an LCD, an LED-Display, OLED-Display, an EPD, or as an electrophoretic display, and the like. The output units 35-2, -3, and -4, are configured to control the display units to display different characters or symbols in dependence on the indicator determined by the calculation section 33. For example, a first character (e.g. "A" as shown in FIG. 2B, or "1" as shown in FIG. 2C) may be displayed whenever the indicator is above some given threshold value, whereas a second character (e.g. "B", or "Z", or "0") may be displayed whenever the indicator is below some given threshold value. In FIG. 2D, no alphabetical or numerical character is used but a more general symbol in the form as, for example, an arrow pointing upward, downward or horizontal, or other symbols such as emoticons and/or so-called smileys. Likewise, the output unit 35-2, -3, or -4 may calculate a trend and control the display accordingly as described in conjunction with FIG. 2A.

FIG. 2E shows a schematic view of a display unit 40-5 that is controlled by a respective output unit 35-5. The display unit 40-5 includes a general purpose display 40-50 in the form of an LCD, LED-Display, OLED-Display, EPD, electrophoretic display, and the like. The output unit 35-5 is here configured to control the display unit 40-5 so as to display a graph 40-51 whose appearance is dependent on the indicator and its evolvement over time. For example, an upward direction of the graph 40-51 may be displayed whenever the indicator is above some given threshold value, whereas a downward direction may indicate that the indicator is below some given threshold value. In particular embodiments, no further elements are displayed so that the information conveyed can be understood only by knowing operators. A similar embodiment is shown in FIG. 2F, where the output unit 35-6 controls a display unit 40-60 to display a bar graph 40-61 on a general purpose display 40-60.

FIG. 2G shows a schematic view of a display unit 40-7 that is controlled by a respective output unit 35-7. The display unit 40-7 includes a general purpose display 40-70 in the form of an LCD, LED-Display, OLED-Display, EPD, electrophoretic display, and the like, to display a classical "speedometer" in the form of a scale 40-71 and a hand 40-72. Naturally, the display unit 40-7 may also be embodied as a physical actual instrument in the form of an analogue meter. The output unit 35-7 is here configured to control the display unit 40-7 so as to control the hand 40-72 to move in relation to the indicator, which, in turn, conveys to the operators that usage/consumption is sufficient or not. Additionally, the scale 40-71 may be complemented by colored ranges (e.g. red and green) conveying to the operators that consumption is satisfactory (e.g. hand 40-72 pointing to a green area, e.g. on the right), or that consumption should be increased (e.g. hand 40-72 pointing to a red area, e.g. on the left).

Figure 3:
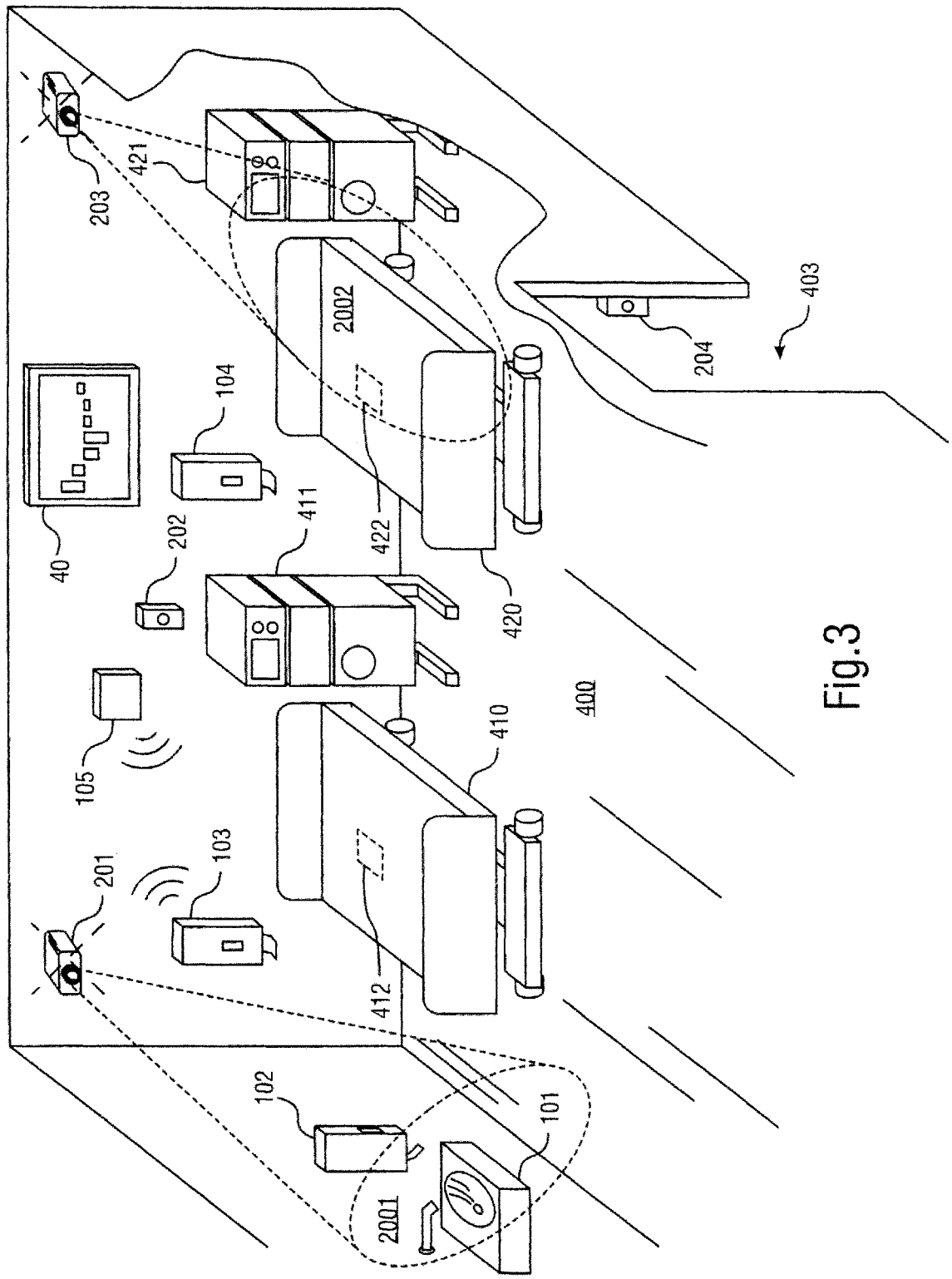
FIG. 3 shows a schematic view of a deployment of an embodiment of a display system.

FIG. 3 shows a schematic view of an example of a deployment of a display system. As an example, there is shown as a facility an intensive care unit 400 with corresponding intensive care points: first and second patient stations 410, 420 and first and second patient care equipment 411, 421. As can be seen, the intensive care unit 400 may be occupied by one or two patients in the shown configuration, whilst other embodiments include other intensive care units with any number of patients and personnel and/or other facilities as mentioned elsewhere in the present disclosure.

In general, however, the number of actually occupied intensive care points (beds) as well as other information (e.g. on a number of individuals working/visiting, on a shift, a time of day, a day of week, a holiday) can be considered as optional metadata M, likewise stored, for example, in the database of FIG. 1. Further examples include information on a type of care given (intensive, orthopedic, surgery, child, emergency, ear/nose/throat, etc.), size of ward/floor/unit in terms of number of beds and/or number of staff, time and date, number of staff working the specific time also divided by staff category (cleaners, nurses, doctors etc.), outdoor weather, cleaning records, and data measured by corresponding equipment (e.g. a pressure/weight sensor in a bed to indicate if there is a patient in the bed or not). Said metadata M can thus contribute in the calculation section 33 when determining the function F and/or contribute when estimating the compliance metric based on the function F and the current usage and second opportunity data U, O. For example, the metadata M can contribute in rendering the function F sensitive to the actual environment (e.g. beds occupied or not) so that it can produce an improved estimate Ce for situations when all or most beds are occupied and when only some beds are occupied.

In an embodiment, the metadata M contributes to the accuracy of the function F in a way that specific scenarios of metadata M and opportunity data O and/or user data U and correspond to respective opportunity scenarios. For example, the metadata M is obtained through receiving signals from pressure (or heat) sensors 412, 422. If one or more of such sensor signals indicate that a corresponding patient station 410, 420 is in use, the opportunities for the use of hygiene equipment will accordingly change. For example, an algorithm may correlate signals from the vicinity sensor 202 and the sensors 412, 422, in a way that signals that indicate an activation of the vicinity sensor 202 (i.e. operator present) and a first pressure sensor 412 correlate to opportunities only in connection with the first patient station 410, whilst signals that indicate an activation of the vicinity sensor 202 and the first pressure sensor 412 and the second pressure sensor 422 correlate to opportunities in connection with both patient stations 410, 420. Accordingly, the parameters of the function F may be compiled in the way that the metadata influences the opportunity scenarios. This is schematically depicted in FIG. 5B, where an optional step S15 includes receiving of the metadata during learning, e.g. when the function and/or its corresponding parameters is/are determined.

The configuration shown in FIG. 3 may be representative for a first learning phase during which the system acquires usage data from an equipment sensor arrangement provided for one or more of the individual pieces of hygiene equipment, such as the soap dispenser 102, the first and second disinfectant dispensers 103, 104, and the hand washing sink 101. In this way, the system is able to receive usage data U from these pieces of equipment 101-104 as possibly individual signals from each corresponding device/sensor. During this phase, also an opportunity sensor arrangement is provided in the intensive care unit 400 that includes one or more cameras 201, 203, a vicinity sensor 202, and a door passing sensor 204. Thereby, the first camera 201 may be in particular arranged for detecting an opportunity in a dedicated area, such as the surrounding area 2001 of the hand wash sink 101. For example, the image and/or video data obtained from first camera 201 may be processed or analyzed for determining whether an individual could/should have used the soap dispenser 102 when washing his/her hands at sink 101. In a way, the use of the sink 101 implies also an opportunity to use the soap dispenser 102. However, the configuration as shown in FIG. 3 is only to be seen as an application example, but is also applicable to configurations different from the environment of an intensive care unit in particular, or from a hospital in general.

Similarly, second camera 203 may observe a further dedicated area 2002 that covers the vicinity and area of second patient station 420, which can be, for example, a bed. In an example, the corresponding image and/or video data from the second camera 203 may be processed or analyzed in order to find an individual entering the area of the second patient station 420 and/or determining the duration and time for how long the individual remains in the vicinity thereof. This could likewise imply an opportunity to use the first disinfectant solution dispenser 104 before or at the early stage of entering the area 2002 that covers the vicinity and area of the second patient station 420. Such visual determination of an opportunity by images and/or a human observer may also be selected for opportunities that are difficult to detect by sensors, such as a healthcare worker performing an aseptic task (WHO moment Nr. 2) or after a body fluid exposure risk (WHO moment Nr. 3). It may be preferable to further consider that WHO moments Nr.s 1 & 5 may be correlated to moments 2 & 3, which can be exploited for removing sensors that either sense moments 1 & 5 or 2 & 3 in the second opportunity sensor arrangement. Such correlations may also be made automatically by the machine learning algorithm.

Likewise, a vicinity sensor 202 may determine the opportunity to use the second disinfectant dispenser 104 when an individual operates first patient care equipment 411 which, in turn, can indicate that manual operations or actions are carried out to patient in first patient station 410, which can be, for example, a bed. In general, any one of the equipment sensors and opportunity sensors may convey signals in any suitable manner, such as by wire-bound communication or wireless communication as, for example, shown between the first disinfectant dispenser 103 and a wireless data acquisition and collection point 105.

As already mentioned, however, the use of first and second cameras 201, 203, or in general a complex opportunity sensor arrangement, may be problematic for various reasons. For example, the analysis and processing of the corresponding and produced image or video data may be expensive, since, for example, sufficiently powerful image processing hardware needs to be employed or a human operator may need to view the image data so as to "manually" determine the corresponding opportunity data. Furthermore, the use of such cameras may require the consent of individuals and personnel being present or active in the intensive care unit 400. At the same time, however, it may be tolerable that cameras are installed for a limited time so that the more expensive opportunity sensor arrangement can be deployed for an initial learning phase, when a calculation section of the system determines a function F based on usage data received from the hygiene equipment 101, . . . and the opportunity data from the first opportunity sensor arrangement including also at least the first and second cameras 201, 203.

At a later (operation) stage, the deployed opportunity sensor arrangement may be reduced in the sense that some individual pieces of opportunity sensor equipment is removed and/or deactivated, or the opportunity sensor equipment is removed completely. For example, at a second phase, the first and second cameras 201 and 203 may be unmounted so that a specific consent to individuals and or personnel in the context of video surveillance may no longer be necessary. Likewise, any expensive or burdensome analysis of the corresponding image or video data may no longer be necessary. At the same time, however, a somewhat reduced opportunity sensor arrangement remains active within the intensive care unit 400 as, for example, consisting only of the vicinity sensor 202 and the door passing sensor 204. In this embodiment, the opportunity sensor arrangement may be a direct reduction from a previously installed opportunity sensor arrangement. Furthermore, metadata sensors may be still employed, such as a pressure/weight sensor 412, 422 for determining whether a bed is occupied or not.

In an embodiment, the method includes estimating a compliance metric from the usage data that may still be available to a high degree of completeness and, optionally, a reduced opportunity data received only from the vicinity sensor 202 and door passing sensor 204 and/or metadata, from the function F that was previously determined based on the usage data and the more comprehensive opportunity data when the first and second cameras 201 and 203 were still operative.

In an embodiment, the system includes a display unit 40 which is controlled by an output section (not shown) as described elsewhere in the present disclosure in greater detail. Specifically, the display unit 40 is arranged so as to convey display data to one or more operators of the hygiene equipment. In a way, a closed loop is provided when it is considered that one or a group of operators use hygiene equipment, this use is detected by respective sensors and fed to a receiving section, the received usage data is assessed and evaluated with regard to an indicator, this indicator determines the display data, which, eventually is again conveyed to the operators of the hygiene equipment:

OPERATOR→HYGIENE EQUIPMENT→SENSOR→USAGE DATA→
→INDICATOR→DISPLAY DATA→DISPLAY→OPERATOR

As a consequence, a technical closed loop system is provided that is able to influence the operator so that the use of the hygiene equipment is promoted.

FIGS. 4A and 4B show schematic views in conjunction with a neural network being used for determining a function. In a way, the employment of a neural network is one way of determining the function as a product of a machine learning procedure. Specifically, FIG. 4A schematically shows a node (neuron) 331 of a neural network. As is known, the neuron 331 has one or more inputs 332 and one output 333. In general, the neuron 331 receives input values $\alpha_{ij}$ at the corresponding input 332, multiplies each input value $\alpha_{ij}$ by a corresponding coefficient $w_{ij}$ and forms the corresponding sum $\beta_j = \Sigma_i w_{ij} \times \alpha_{ij}$ at the output 333. Furthermore, the output $\beta_j$ could also be normalized to a value between 0 and 1, or be made binary so that it either assumes 0 or 1 ($\beta_j \in \{0, 1\}$) by means of applying a rounding and/or Heavyside function. As then shown in FIG. 4B, a neural network 334 is composed of a corresponding manifold of neurons 331 as one is individually shown in FIG. 4A. As a consequence, the network 334 provides at the bottom a number (e.g. k) of inputs 332' receiving the $\alpha_{k1}$ (at k inputs) and, after one or more hierarchy levels of individual neurons 331, at the output 333' the output $\beta_l$ of the topmost neuron of the network 334.

According to an embodiment, the calculation section of the system employs such a neural network 334 for determining the compliance metric. In such embodiments, the neural network 334 may be operated with usage data only and opportunity data and meta data are optional. In other words, the system operates from a function F that was initially trained during a learning phase using user data U, opportunity data O, and, optionally, meta data M. Since during a learning phase both the user data U and the opportunity data O can be directly correlated to a specific compliance metric Cc (e.g. a use rate derived from U divided by an opportunity rate derived from O), the neural network 334 can be trained with this data to determine the coefficient $w_{ij}$. In other words, the $w_{ij}$ are trained so that the network 334 gives the correct Cc at output 333' for the given U, O, and, optionally, M. It is noted that in the context of the present embodiment, a group of or the entirety of the determined coefficients $w_{ij}$ corresponds to the function F as mentioned elsewhere in the present disclosure. In other words, the neural network 334 with the trained coefficients $w_{ij}$ represents the function F in this embodiment.

The present embodiment then envisages to employ the trained neural network 334 (function) to determine at the output 333' a value Ce of an estimated compliance metric based on a second set of data 336 that at least comprises user data U collected during operation and only optionally opportunity data and meta data.

In the operation phase, the function F can then be employed to provide the compliance metric Ce from at least the usage data so as to be an accurate estimate to a corresponding "true" or "complete" compliance metric Cc. However, since the function F is now trained and the corresponding parameters have been learned, an algorithmic implementation would need to evaluate the mentioned inputs with the learned parameters. The latter learned parameters provide that the output compliance metric Ce is calculated taking into account the learned correlations and that the output is an accurate mapping of the compliance metric Cc even without the availability of opportunity data O. In other words, FIGS. 4A and 4B may relate to the two process steps, namely the training step which calculates the F in an iterative process between the "complete" initial set of learning data 335 in relation to a known Cc (at the top of the triangle), and an operational step which uses the known F (in the triangle) which calculates (or estimates) an estimated Ce with the aid of the "incomplete" set of data 336.

FIG. 5A shows a flowchart of an embodiment of a general method. This general method embodiment is for displaying an indicator of a usage of hygiene equipment by one or more operators, and includes a step S1 of receiving usage data from an equipment sensor arrangement, said usage data indicating a usage of said hygiene equipment, a step S2 of determining, based on the received usage data said indicator, and a step S3 of providing display data to a display unit based on said indicator, said display unit being arranged so as to convey said display data to said one or more operators.

With reference to FIG. 5C, a flowchart of an example of a way to employ the learned function. In step S21, usage data "U" is received. Optionally and either sequentially or concurrently also opportunity data and/or meta data is received in step S22 (note that the depicted order may likewise be reversed for sequential reception so that the opportunity/meta data is received prior to receiving the usage data). Since this embodiment considers that the function F (or its corresponding parameters) is already trained, it can now be referred to this function in step S23, and the compliance metric Ce can be calculated in step S24 by, for example, computationally evaluating the function:

$$Ce=F(U[,O][,M]),$$

where [, O] and [, M] mean that the consideration of O and/or M are optional.

In a step S25, the display data can be generated in line with any suitable embodiment as some of these have been described in conjunction with FIGS. 2A to 2G, and in the step S26, the display system or a display device can be controlled accordingly so as to appear in line with these embodiments. In this way, a feedback loop is closed by providing the same operator who uses the hygiene equipment with information on usage of the hygiene equipment.

FIG. 5D shows a flowchart of a general method for both determining the function as well as evaluating it for determining the compliance metric. The method embodiments can be implemented for displaying a compliance metric indicating the usage of hygiene equipment by one or more operators. Generally, the involved methods may consider a first set of steps: a step S111 of receiving usage data from an equipment sensor arrangement, said usage data indicating a usage of said hygiene equipment; a step S121 of receiving opportunity data from an opportunity sensor arrangement (and optionally meta data), said opportunity data indicating a set of opportunities to use said hygiene equipment; and a step S130 of determining, based on said usage data received in the step S111 and the opportunity data (and optionally the meta data), a function for estimating said compliance metric from at least the usage data. These steps may be identified as being part of a "learning phase" during which a opportunity arrangement is available and during which the function is determined.

The determined function can be then employed during an "operation phase". Such a phase may be associated with a second set of steps: a step S112 of receiving usage data from the equipment sensor arrangement and an optional step S122 of again receiving opportunity (and meta) data from a corresponding opportunity sensor arrangement. In a step S140 it is then estimated the compliance metric from at least the usage data received in the step S112. Additional phases may be envisaged, where the compliance metric estimated by using the function is verified or confirmed, and/or where the function is optimized and/or fine-tuned for the respective purpose.

Generally it may be desirable that the system is trained with the aim of reaching a stable and robust function F. In an additional test phase it can be determined how reliable the F-function is. This is done by exposing the F-function to another, un-seen, set of "complete" data (O, U) to measure how well the estimated compliance Ce matches the "real" compliance Cc. Then, the operation phase can be initiated as described elsewhere in the present disclosure. In this embodiment the "complete" data can be split in two sub-sets of which one is used in the first training/learning phase and the other in the testing phase.

FIG. 6 shows a schematic view of a general entity. The entity can be any collection of processing and memory resources that are suitable for implementing the corresponding sections of a system for estimating the indicator for example in the form of a compliance metric. For example, the entity 30 can be implemented as a stand-alone computer, a server, a processing share of a datacenter, or an application running on some kind of shared hardware. More specifically, in this embodiment, the entity 30 includes processing resources 301 (e.g. CPU), memory resources 302 and communication means 303 (e.g. a receiver/transmitter working according to WLAN, WiFi, WiMAX, Bluetooth™, GPRS, GSM, PCS, DECT, UMTS, 3G/4G/5G, LTE, etc., or a wire-bound standards such as Ethernet and the like) that are configured to communicate with some kind of network 304 (e.g. LAN, wireless communication system, an intranet, the Internet, and the like). By means of the latter, the system is able to receive the usage and opportunity data signals u-i, o-i, etc., access the database 34, or to convey any estimated metric to a given location.

Specifically, the memory resources 302 are adapted to store code that instructs the processing resources 301 during operation to implement at least a first receiving section configured to receive usage data from an equipment sensor arrangement, said usage data indicating a usage of said hygiene equipment, a calculation section configured to determine, based on said usage data an indicator, and an output section configured to provide display data to a display unit based on said indicator, said display unit being arranged so as to convey said display data to said one or more operators. Naturally, the code may be adapted so as to implement any other modification envisaged by the embodiments of the present invention.

Although detailed embodiments have been described, these only serve to provide a better understanding of the invention defined by the claims and are not to be seen as limiting.

The invention claimed is:

1. A system for displaying an indicator of a usage of hygiene equipment by operators, the system comprising:
    more than one hygiene equipment device;
    a display arranged in a vicinity of at least one of said hygiene equipment devices; and
    at least one memory including instructions, when executed by at least one processor, to perform the method comprising:
        receiving usage data from an equipment sensor arrangement including at least one sensor per hygiene equipment device, said usage data indicating a usage of said hygiene equipment devices by said operators;
        determining, based on said usage data, an indicator of the usage of the hygiene equipment devices by said operators; and
        providing display data representing level of usage by said operators to said display based on said indicator, said display being arranged so as to convey said display data automatically to at least one of said operators.

2. The system according to claim 1, wherein the system is configured to determine as said indicator a compliance metric indicating a usage of the hygiene equipment versus opportunities of using said hygiene equipment.

3. The system according to claim 2, wherein the system is further configured to receive opportunity data from an opportunity sensor arrangement, said opportunity data indicating a set of opportunities to use said hygiene equipment, wherein the system is configured to determine the compliance metric based on said usage data and the opportunity data.

4. The system according to claim 1, wherein the system is further configured to receive meta data, wherein the system is configured to determine the indicator further based on the meta data.

5. The system according to claim 1, wherein the display is arranged on a wall.

6. The system according to claim 1, wherein the system is configured to provide the display data using a comparing of the indicator to a predetermined threshold value.

7. The system according to claim 1, wherein the system is configured to provide the display data using a variation of the indicator over time.

8. The system according to claim 1, wherein the system is configured to provide the display data for instructing the display to change a displayed color.

9. The system according to claim 1, wherein the system is configured to provide the display data for instructing the display to change a displayed character or symbol.

10. The system according to claim 1, wherein the system is configured to provide the display data for instructing the display to display a graph.

11. The system according to claim 1, wherein the hygiene equipment comprises a soap dispenser, a dispenser for disinfectant solutions, gels or substances, a towel dispenser, a glove dispenser, a tissue dispenser, a hand dryer, a sink, a tap, or a radiation assisted disinfectant point.

12. The system according to claim 1, wherein the system further comprises a database arranged to store usage data.

13. The system according to claim 1, wherein said usage data further indicates information on when the piece of hygiene equipment was used, where the piece of hygiene equipment was used, information on how much of the dispensed substance was used, information on who was using the piece of hygiene equipment, or information on what was used if the piece of hygiene equipment is a multi-dispenser containing.

14. The system according to claim 3, wherein said opportunity data further indicates information on when the piece of hygiene equipment could have been used, where the piece of hygiene equipment could have been used, information on how much of the dispensed substance could have been used, information on who could have been using the piece of hygiene equipment, or information on what could have been used if the piece of hygiene equipment is a multi-dispenser containing.

15. A method for displaying an indicator of a usage of hygiene equipment by operators, the method comprising:
    at least one processor receiving usage data from an equipment sensor arrangement including at least one sensor per hygiene equipment device, said usage data indicating a usage of said hygiene equipment devices by said operators;
    said at least one processor determining, based on the received usage data, an indicator of the usage of the hygiene equipment devices by said operators; and
    said at least one processor providing display data representing level of usage by said operators to a display based on said indicator, said display being arranged in a vicinity of at least one of said hygiene equipment devices and arranged so as to convey said display data automatically to at least one of said operators.

* * * * *

UNITED STATES PATENT AND TRADEMARK OFFICE
CERTIFICATE OF CORRECTION

PATENT NO. : 10,977,925 B2
APPLICATION NO. : 16/303269
DATED : April 13, 2021
INVENTOR(S) : Hakan Lindstrom et al.

It is certified that error appears in the above-identified patent and that said Letters Patent is hereby corrected as shown below:

In the Specification

Column 1, Line 51, reads "for 140.000 patients/year, affecting millions more and costs" and should read -- for 140,000 patients/year, affecting millions more and costs --.

Column 2, Line 42, reads "ment the hygiene scheme as good as possible so as to reduce" and should read -- ment the hygiene scheme as well as possible so as to reduce --.

Column 10, Line 34, reads "metadata M and opportunity data O and/or user data U and" and should read -- metadata M and opportunity data O and/or user data U --.

Column 12, Line 3, reads "individual pieces of opportunity sensor equipment is" and should read -- individual pieces of opportunity sensor equipment are --.

Column 13, Line 61, reads "a way to employ the learned function. In step S21, usage" and should read -- a way to employ the learned function is shown. In step S21, usage --.

In the Claims

Column 16, Claim 13, Line 36, reads "multi-dispenser containing." and should read -- multi-dispenser. --.

Column 16, Claim 14, Lines 44-45, read "used if the piece of hygiene equipment is a multi-dispenser containing." and should read -- used if the piece of hygiene equipment is a multi-dispenser. --.

Signed and Sealed this
Seventh Day of December, 2021

Drew Hirshfeld
*Performing the Functions and Duties of the*
*Under Secretary of Commerce for Intellectual Property and*
*Director of the United States Patent and Trademark Office*